(12) United States Patent
Pijls

(10) Patent No.: US 7,858,028 B2
(45) Date of Patent: Dec. 28, 2010

(54) PASTEURIZING OR STERILIZING

(75) Inventor: Thomas Ferdinand A. Pijls, Malden (NL)

(73) Assignee: Nutricia N.V., Zoetermeer (NL)

( * ) Notice: Subject to any disclaimer, the term of this patent is extended or adjusted under 35 U.S.C. 154(b) by 201 days.

(21) Appl. No.: 10/601,009

(22) Filed: Jun. 17, 2003

(65) Prior Publication Data

US 2004/0057867 A1 Mar. 25, 2004

Related U.S. Application Data

(63) Continuation of application No. PCT/NL01/00935, filed on Dec. 21, 2001.

(30) Foreign Application Priority Data

Dec. 22, 2000 (NL) .................................. 1016981

(51) Int. Cl.
| | |
|---|---|
| A61L 2/08 | (2006.01) |
| B01J 19/00 | (2006.01) |
| A23L 3/16 | (2006.01) |
| C12C 7/28 | (2006.01) |
| F16K 11/00 | (2006.01) |
| A23C 3/02 | (2006.01) |
| B02C 25/00 | (2006.01) |
| B01D 47/06 | (2006.01) |

(52) U.S. Cl. ................ 422/26; 422/1; 422/41; 422/307; 426/407; 426/520; 426/521; 426/522; 137/241; 137/238; 99/452; 99/453; 99/483; 99/484; 99/485; 99/511; 99/747; 99/486; 99/517; 261/78.1; 261/78.2; 261/DIG. 10; 261/DIG. 76

(58) Field of Classification Search .............. 422/1, 422/26, 41, 307; 426/407, 520–522; 137/241, 137/238; 99/452–453, 483–485, 511, 747, 99/486, 517; 261/78.1–78.2, DIG. 10, DIG. 76
See application file for complete search history.

(56) References Cited

U.S. PATENT DOCUMENTS

| | | | | |
|---|---|---|---|---|
| 2,401,077 | A | * | 5/1946 | Johnston .................... 426/511 |
| 3,564,723 | A | * | 2/1971 | Passey ........................ 34/443 |
| 3,843,828 | A | * | 10/1974 | Arndt ......................... 426/585 |
| 3,925,560 | A | * | 12/1975 | Scott et al. ..................... 426/2 |

(Continued)

FOREIGN PATENT DOCUMENTS

CH    GB 2 036 534 A * 7/1980

(Continued)

OTHER PUBLICATIONS ehow.com Internet printout, "How to Prepare Ready-to-Mix Powdered Baby Formula", 1999.*

(Continued)

*Primary Examiner*—Jill Warden
*Assistant Examiner*—Monzer R Chorabaji

(57) ABSTRACT

The invention relates to a method for preparing a product having a low content of microorganisms by using steam. A method according to the invention can be used to pasteurize or sterilize a product, while retaining the activity of one or more active substances that may be present in the product, and relates to a method wherein a product is dried with air. Furthermore, the invention relates to a product obtainable according to a method according to the invention.

23 Claims, 1 Drawing Sheet

U.S. PATENT DOCUMENTS

Figure 1:
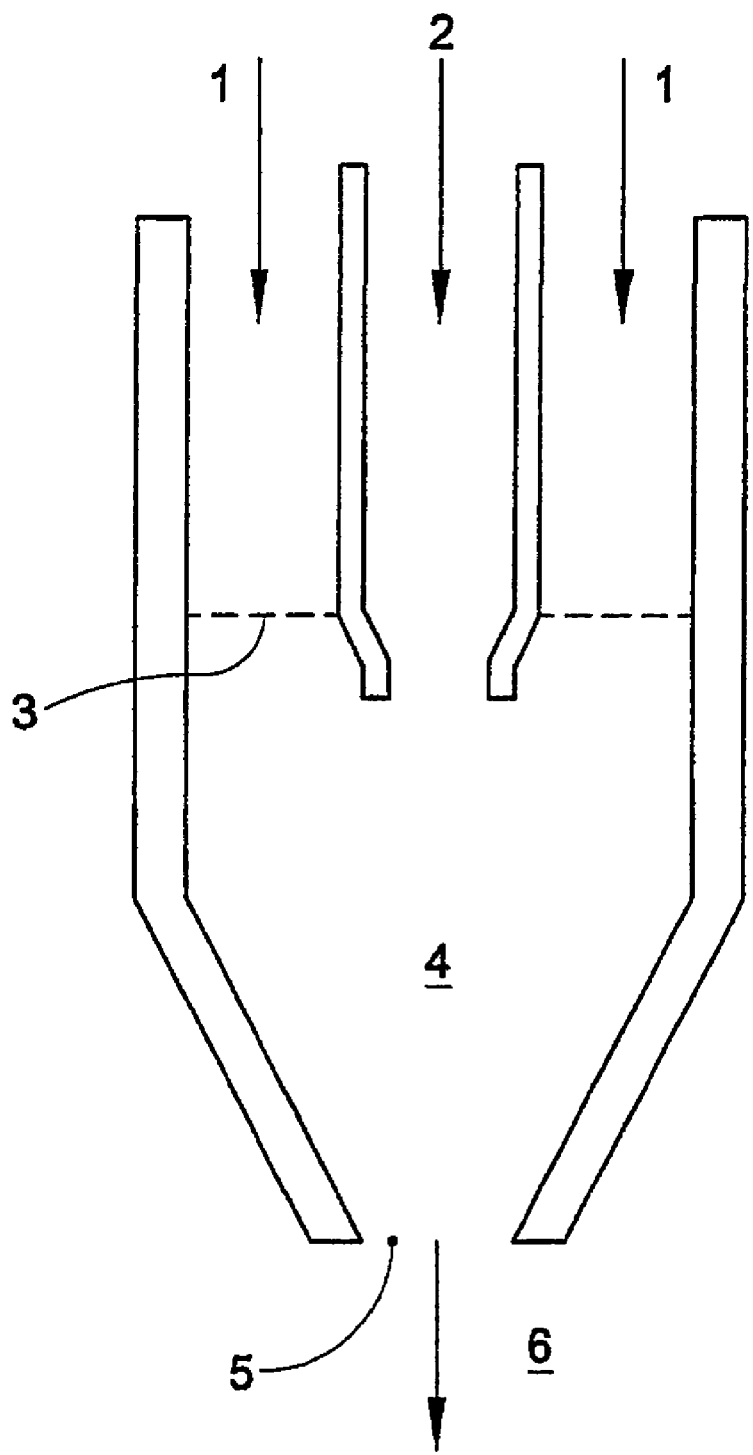

| | | | |
|---|---|---|---|
| 3,927,974 A | | 12/1975 | Johansson et al. |
| 4,062,641 A | * | 12/1977 | Hovmand et al. ............... 425/6 |
| 4,091,003 A | * | 5/1978 | Bosund et al. ............... 530/416 |
| 4,096,287 A | | 6/1978 | Kemp |
| 4,141,783 A | * | 2/1979 | Pisecky et al. ................. 159/45 |
| 4,265,702 A | | 5/1981 | Prudhon et al. |
| 4,280,851 A | | 7/1981 | Pitchon et al. |
| 4,281,024 A | | 7/1981 | Hauberg et al. |
| 4,600,472 A | | 7/1986 | Pitchon et al. |
| 4,689,237 A | * | 8/1987 | Fabre .......................... 426/521 |
| 4,724,620 A | * | 2/1988 | Hsu ............................ 34/174 |
| 4,787,304 A | | 11/1988 | Bronnert |
| 4,851,250 A | | 7/1989 | Bronnert |
| 5,149,799 A | | 9/1992 | Rubens |
| 5,210,958 A | * | 5/1993 | Bond et al. .................... 34/422 |
| 5,395,569 A | | 3/1995 | Badertscher et al. |
| 5,558,819 A | * | 9/1996 | Den Hollander ............. 261/21 |
| 5,620,733 A | | 4/1997 | Chaveron et al. |
| 5,980,375 A | | 11/1999 | Anderson et al. |

FOREIGN PATENT DOCUMENTS

| | | |
|---|---|---|
| EP | 0 438 783 | 7/1991 |
| EP | 0 446 984 | 9/1991 |
| EP | 0 617 897 A1 | 10/1994 |
| GB | 2 036 534 | 7/1980 |
| SU | 982 637 A1 | 12/1982 |
| US | EP 0 438 783 A2 * | 7/1991 |
| WO | 98/07328 A2 | 2/1998 |
| WO | 99/39593 A1 | 8/1999 |
| WO | WO 00/56161 | 9/2000 |

OTHER PUBLICATIONS

Brazhnikov et al., "Egg Powder Production includes evaporation of egg mass followed by spray-drying and thermal treatment for storage stability," Russian Pat. No. SU-982637. Abstract only. #XP-002173623, (1983).

International Search Report issued May 2, 2002 for PCT/NL01/00935 (WO 02/051266).

* cited by examiner

PASTEURIZING OR STERILIZING

This application is a continuation of pending prior international application number PCT/NL01/00935, filed on Dec. 21, 2001; which claims priority from Netherlands patent application number NL 1016981, filed Dec. 22, 2000; both of which are hereby incorporated herein by reference.

The invention relates to a method for preparing a product having a low content of microorganisms, to a method for drying such a product, and to a product obtainable according to a method according to the invention.

The microbiological quality of products intended for consumption, such as, for instance, infant food, has to comply with strict requirements. This quality is guaranteed by taking a number of measures. Thus, inter alia pure ingredients are used, any source of infection has to be prevented, and the product is subjected to a heat treatment, so that the present microorganisms and/or spores thereof are killed.

Such a heat treatment may take place by using steam, as is known from DE 29 46 326 and EP 0 601 329. Described therein are T-shaped bodies, which enable the user to bring steam into intensive contact with a flow of liquid product. Sterilization takes place, because the steam is properly mixed with the product and the product maintains a high temperature for a relatively long time. Because of this, however, heat-sensitive components in the products are damaged, and undesirable organoleptic changes could take place in the product.

Because of damage to heat-sensitive substances in a product, for instance as a result of irreversible denaturation, polymerization, decomposition, oxidation etc., these heat-sensitive substances may lose their activity, and even undesirable compounds could be formed, such as, for instance, Maillard products and polymerization products.

Also, the heating of, for instance, specific protein- or starch-containing products and slurries of products having a high viscosity may cause great practical problems, such as blockage of supply channels or fouling of heat exchangers, which may have disastrous consequences to the efficiency of a pasteurization or sterilization process and other processing steps, such as, for instance, the drying of a pasteurized product.

An object of the present invention is to provide a method for preparing a product having a microbiological quality good enough for inter alia consumption purposes, under conditions irreversibly affecting the product as less as possible.

Surprisingly, it has been found possible to prepare a pasteurized or sterilized product having high quality and, in particular, a high biological activity, by means of a method wherein a product in liquid form is introduced into a heated mixing chamber and is atomized while admixing steam, so that microorganisms are killed.

As referred to herein, pasteurizing and sterilizing is the exposure of the product to a high temperature for a suitable duration, so as to inactivate specific enzymes and kill microorganisms, such as yeast, molds and pathogenic bacteria, and spores of microorganisms, so that the microbiological quality of the dried product is improved. Sterilization is a thermal treatment under conditions generally leading to a greater degree of killing of microorganisms than pasteurization.

The microbiological quality is expressed in the form of the germ count. This is the number of germs (i.e. microorganisms and spores thereof) per unit of product and can be determined by means of a known per se measuring method, for instance by taking a representative sample of the product, optionally diluting and plating it. The number of colonies of microorganisms can then be counted. There are also automatic systems in which the number of microorganisms is counted and measuring systems in which by means of a coloring agent reacting to the amount of microorganisms the number of germs is determined.

As referred to herein, a liquid form is a flowable form, such as a liquid, a homogeneous solution containing one or more solids, a spray of droplets, but also a heterogeneous mixture (slurry) of one or more solids, in which not all the solid or solids need to be dissolved completely. Examples of slurries are emulsions, suspensions, dispersions, and the like. It is an advantage of a method according to the invention that, as a result of the short heat treatment during sterilization and especially when pasteurizing, more stable emulsions can be prepared. Moreover, it is possible in a method according to the invention to pasteurize or sterilize, and optionally dry, plant extracts. A special advantage of a method according to the invention is that it is particularly suitable to kill germs in plant extracts, while volatile compounds, such as vegetable oils, remain in the product for a substantial part. Thus, for instance, the invention is very suitable for the treatment of valerian extracts, such as a water or ethanol extract in which thermolabile valepotriates and volatile oils, such as valeric acids, are better preserved than with conventional processes, but also for the treatment of alcoholic ginger extracts containing zingiberene. Moreover, it has been found that, for instance, green tea extracts can be excellently dried, while a smaller degree of polymerization of polyphenols occurring than with conventional processes.

As referred to herein, a solid is a substance that, in dry condition at the ambient temperature, is in a solid phase, including a crystalline or an amorphous phase.

As referred to herein, the solid content of a substance is the amount of solid that, dissolved or admixed (for instance, dispersed or emulsified), is contained in a composition.

As referred to herein, an average particle diameter is the number average.

The invention proves to be very suitable for obtaining a pasteurized or sterilized product having a good microbiological quality, while, moreover, in comparison with comparable conventional techniques, the activity, the solubility and/or the structure of heat-sensitive substances, if present, are better preserved.

A substance is regarded as heat-sensitive, if the substance in a product to be pasteurized, after a standard pasteurization treatment of 20 seconds at a temperature of 82° C., has irreversibly changed in a substantial degree relative to the mentioned substance in the mentioned product without this heat treatment. This change could be determined, for instance, on the basis of a measurement of the physicochemical properties of the product or on the basis of a change of a specific biological activity. A simple method for determining whether a substance is heat-sensitive is the measurement of changes in the solubility of the substance before and after heat treatment. Such a method for dairy proteins is, for instance, the determination of the degree of denaturation before standard pasteurization and after standard pasteurization by bringing a sample of the protein-containing product into a solution (for instance, leading to a solution with 10 weight percent product) of a buffer having a pH of 4.6, so that denatured and agglomerated proteins precipitate. After centrifugation, the amount of protein in the resulting pellet of denatured and/or agglomerated product and in the solution with the native protein can be determined. After the above-mentioned standard pasteurization, heat-sensitive proteins will be disappeared from the solution typically to at least 20%.

Examples of such heat-sensitive substances are peptides (including oligo- and polypeptides), such as, for instance, growth hormones, proteins, immunoglobulins, enzymes, specific fatty acids, cytokines, vitamins, antioxidants, such as, for instance, polyphenols, minerals, hormones, steroids, some polysaccharides, sugars, valepotriates (as occurring in valerian), zingiberene (for instance, from ginger) and specific complex lipids. Moreover, volatile substances are reckoned among the heat-sensitive substances, because under the influence of heat they need not per se undergo chemical changes though, but tend to evaporate from a product. Examples of such volatile substances are volatile oils, which may be present in, for instance, plant extracts, such as valeric acids present in a polar extract of valerian.

Thus, with the method it proves possible to prepare a product having a high content of one or more heat-sensitive substances, in an active or activable form, so that the (intrinsic) biological activity of such a heat-sensitive substance can be preserved. Thus, for instance, it turns out that in a product pasteurized according to the invention immunoglobulin can retain more than 80% of its activity. Also in a product sterilized according to the invention, the activity of one or more heat-sensitive substances will be preserved better than in a product sterilized in a conventional manner, certainly as regards a moderately thermolabile substance and an only slightly heat-sensitive substance.

An activable form is, for instance, a compound in a product that, during the processing of the product, undergoes a conformation change, but is again in an active conformation when the product is finally used.

In the case of, for instance, whey proteins, but also with other polypeptides, when heating, in the first instance unfolding of the molecules generally occurs (a conformation change or denaturation), which is still reversible, and then (irreversible) polymerization of these heat-sensitive molecules may occur, in which undesirable aggregates are formed. Because it has been found possible with a method according to the invention to effectively pasteurize or sterilize through a short and rapid heating, the molecules, such as whey proteins, will therefore not polymerize or polymerize to a much lesser degree, so that no or much smaller agglomerates are formed. Consequently, a pasteurized or sterilized product may not only contain one or more heat-sensitive substances with a better preserved activity, solubility and/or molecular, but also macroscopic structure, but also have a more desirable structure, and the low content of aggregates ensures a reduced need for maintenance of the device in which the method is carried out. In fact, the risk of blockages in the pasteurization or sterilization system or efficiency reductions of heat exchangers, if present, as a result of caking of protein or other agglomerates is strongly decreased through a method according to the invention.

Also, a method according to the invention for pasteurizing a product comprising a mixture of liquids or an emulsion has the advantage that through the very short heating less breaking or no breaking at all occurs.

A method according to the invention proves to be very suitable for preparing a product while retaining the desired activity with a very good microbiological quality, while the aerobic germ count per gram of dry product at 30° C. is less than 10,000, and preferably less than 5,000, in at least four of five representative samples that are analyzed. The aerobic germ count per gram of product at 55° C. will be less than 1,000, and preferably less than 500, in at least four of the mentioned five samples.

Because of the effective sterilization or pasteurization and the preservation of heat-sensitive substances in a desired form, the invention is very suitable for a wide range of products. Examples of products preferably obtainable by using a method according to the invention are (complex) foods containing heat-sensitive substances, such as infant foods or sports foods, and biological substances, such as egg products, plant extracts, milk, whey, but also blood, and preparations into which these ingredients are processed, and which contain, for instance, one or more heat-sensitive peptides and/or proteins, such as specific immunoglobulins, growth factors and/or other hormones, and/or other heat-sensitive substances, such as vitamins and/or polyphenols.

Sterilization is preferably applied to products that need to have a very long shelf life. Moreover, it may be preferred to apply sterilization to products for consumers suffering from poor health, for whom it is especially important to obtain a product having a lowest possible germ count because of their possibly less properly functioning immune system. Examples of such products are specific foods for patient, such as foods to be administered intravenously, and the like.

As already indicated, pasteurization or sterilization takes place according to the invention by atomizing a product flow with steam in a mixing chamber. Through the high temperature of the steam and the intensive mixing the germ killing takes place rapidly. Preferably, as a result of a turbulent mixing of product flow and steam a fine spray is formed, so that the product present in the spray is rapidly heated. The pasteurization or sterilization proves to proceed efficiently by selecting the conditions such that steam of high temperature is used, and the steam is removed again through flash evaporation. Consequently, a thorough heating of the whole product can take place very rapidly, so that with a short intense heat treatment a better ratio between the degree of germ killing and (irreversible) inactivation of heat-sensitive substances can be realized.

On the basis of the criteria described herein those skilled in the art will be able to make a selection from the mixing chambers known in the art for a specific application. A mixing chamber generally comprises one or more inflow openings for steam flows and for product flows, in which a product flow may optionally be premixed with a part of the steam. For most of the applications it is preferred to select the mixing chamber such that only one product flow is atomized with one steam flow, since this simplifies the cleaning of the mixing chamber after use.

A schematic representation of a suitable nozzle for pasteurization or sterilization according to the invention is shown in FIG. 1, in which a nozzle with mixing chamber is shown. It turns out that a nozzle with mixing chamber can be very effectively used for the pasteurization or sterilization of a product. A suitable mixing chamber is generally characterized in that steam and product to be treated are mixed and atomized, while the volume throughput of the steam will be much greater than that of the product to be treated and the residence time of the atomized product is sufficiently long to obtain a desired degree of germ killing. The volume ratio between the steam flow and the product flow may range between, for instance, about 20:1 and 100:1. It is important that the pressure in the mixing chamber is higher than in the space to which the pasteurized or sterilized product is passed.

The form and size of the inflow openings for the steam flow (1) and the flow of the product in liquid form (2) in the mixing chamber and their mutual position are selected such that intensive mixing takes place between product and steam. It is noted that the inflow openings can be placed such (as shown in FIG. 1) that the steam flow and the product flow enter the mixing chamber in substantially parallel direction. This may take place both horizontally, vertically and diagonally manner. However, it is also possible that the steam flow and the product flow enter the mixing chamber at different angles, for instance a vertical steam flow and a horizontal product flow. The inflow openings are further arranged such that the product is atomized in small droplets, which after a short residence time in the mixing chamber (4) leave the mixing chamber through an outflow opening (5), for instance to a drying chamber (6). The inflow opening(s) for the steam flow preferably contain a steam distribution plate (3). By changing the dimensions of the mixing chamber and/or the outflow opening(s) in the manner known to those skilled in the art, the average residence time and particle size of the atomized droplets can be varied.

The mixing is preferably realized by contacting the product flow and the steam flow close to the inflow opening of the product in the mixing chamber and bringing the steam at high speed around the product, which is thereby broken up into small droplets. In a preferred embodiment, such a mixing takes place by bringing the steam near the product concentrically around the inflow opening of product in the mixing chamber. The product flow to steam flow ratio can be varied within wide ranges. In a preferred embodiment, this ratio is 1.6-10 kg product in liquid form per kg steam. Very good results are moreover realized at a wet product flow to steam flow ratio of 1.75-7 kg product in liquid form per kg steam. In the case of a method in which is pasteurized a mixture comprising a solid or a substance that can solidify by drying (for instance a dispersion), steam is preferably mixed with the product to be pasteurized or sterilized in a product to steam ratio of about 0.7 to 6.5 kg solid per kg steam. In terms of volume flows, depending on the temperature and the prevailing pressure, the volume ratio will strongly depart from the mass ratio.

In principle, any type of mixing chamber is suitable in which steam and product can be mixed and atomized. Very suitable for mixing and atomizing a product-steam mixture according to the invention is a nozzle such as "two-fluid" type nozzle, an example of which is described in EP-B 0 438 783 (see FIG. 1 of EP-B 0 438 783). This nozzle contains a small chamber at the end of a product line in which steam and product are combined. To increase the pasteurization or sterilization capacity, more nozzles can be used in a parallel arrangement.

The temperature of the supplied saturated or superheated steam in a method according to the invention is preferably in the range of 120-250° C., and more preferably between 140° C. and 200° C. In general, the temperature in the mixing chamber will be maintained at the desired level through the steam, although it is also possible that the mixing chamber itself is heated by another heat source.

Good results are obtained when introducing the steam into the mixing chamber at a steam pressure of 3-20 bar, and in particular at a steam pressure of 5-15 bar, in mixing chambers about 1-20 cm in length. This pressure is preferably measured just before the steam is introduced into the mixing chamber via a spray nozzle.

A suitable residence time in the mixing chamber is—depending on the temperature, the product and the required reduction of the number of germs—preferably in the range of 0.2-20 msec, and more preferably between 1 and 10 msec. The temperatures of the steam flow and the residence time in the mixing chamber are selected such that a desired degree of killing of microorganisms takes place. The above-mentioned ranges for the temperature, residence time and other conditions are suitable for pasteurization, but also for sterilization.

The degree of killing of microorganisms may be expressed as decimal reduction. In a preferred embodiment for preparing a pasteurized product, the decimal reduction is at least 2, which means a reduction of the number of microorganisms by a factor of 100. More preferably, the decimal reduction is at least 2.4, still more preferably 2.6 or more. For sterilization of a specific product a higher temperature and/or longer residence time will be adjusted longer than for pasteurization of a similar product to realize a greater degree of germ killing. Preferably, the sterilization leads to a decimal reduction of the number of germs of at least 5 or even 7 or more.

In principle, the invention may also be used for the pasteurization or sterilization of a product in a liquid form having a low solid content, for instance 2-20%, a product having less than 2% solid content or even a liquid in which no solids are dissolved. The invention is not only suitable for products having a low viscosity, but also in particular for the treatment of product flows having a high viscosity to more than 0.5 Pas or even 1 Pas or higher. As referred to herein, viscosity is the dynamic viscosity of the product flow under the conditions prevailing during the method.

Furthermore, it is a special aspect of the invention that the solid content in the liquid form comprising the product may be high, without occurrence of fouling problems, such as blockage. In a preferred embodiment for, for instance, a product comprising proteins, carbohydrates and/or fats, the solid content of the flow that comprises the product and is to be pasteurized or sterilized is more than 45 wt. %. A solid content of the product in liquid form of at least 53 wt. % is even more preferred. Because it is possible to treat a product in liquid form having a high solid content, it turns out that with a method according to the invention energy can be saved. Moreover, a milder, preferably shorter, heat treatment is thus sufficient, so that heat-sensitive components remain better intact.

For an extra rapid cooling of, for instance, a liquid, the liquid product, after the killing of microorganisms, may be injected into a cooling device. For this purpose an expansion vessel (flash system) is very suitable. The rapid cooling enhances an effective pasteurization or sterilization and preservation of (activity of) heat-sensitive substances. Moreover, the resulting product may be passed through a heat exchanger, if so desired.

Moreover, it turns out that a method for the pasteurization or sterilization of a product according to the invention can be excellently combined with further processing of a pasteurized or sterilized product, such as, for instance, drying. Thus, it turns out that a pasteurized or sterilized product in a liquid form comprising one or more solids can be very efficiently dried in one step to obtain a powder through spray drying. Products having a high solid content can be effectively dried, through the invention, provided the product has a suitable viscosity, so as to be flowable and capable of being atomized. Such suitable viscosities are known to those skilled in the art or can be easily determined empirically. Very good results are obtained with products having a viscosity in the range of 0.04 Pas through 1 Pas, in particular with products having a viscosity in the range of 0.05 to 0.7 Pas.

In a preferred method for preparing, for instance, a product comprising a protein, fat, carbohydrate and/or one or more other nutrients, the solid content of the product in liquid form is more than 45%, and more preferably at least 53%.

Dried powdered products, such as nutritious products, are already being prepared on a large scale by spray drying. Spray drying often takes place by injecting a solution of a product to be dried into a space, often as a spray, after which the solvent is evaporated at elevated temperature. For evaporation hot (dry) air is mostly used, which is blown into the drying space in large amounts. Such a method is known from, for instance, EP 0 043 693, in which so-called multi-fluid nozzles are described for spraying a viscous liquid, in particular molasses, for animal feed. A disadvantage of such a method is that compressed dry air often has to be admixed. This requires special expensive apparatus to produce a sufficient amount of sterile air. For this reason such a principle is not often used in, for instance, the dairy industry.

EP-B 0 438 783 describes a two-fluid nozzle, through which an amount of steam and starch in water is passed, while during spraying under the proper conditions the starch can be gelatinized to a substantial degree, after which the starch is dried.

The combination according to the invention of pasteurization or sterilization and drying has process-economical, but also qualitative advantages. In a conventional process management, in which a pasteurization/sterilization device and a drying device are used separately, fouling of the heat exchanger of the drying device often occurs through denaturation of active substances. This phenomenon is substantially fully excluded in a combined pasteurization/sterilization and drying treatment. It is therefore preferred in a combined pasteurization/sterilization and drying treatment according to the invention that the pasteurization or sterilization carried out in a pasteurization/sterilization nozzle according to the invention is substantially the only pasteurization or sterilization step in the whole product preparation.

The pasteurized or sterilized product may be conventionally dried, like in a fluid bed-drying device, but it has also been found possible that the atomized pasteurized or sterilized steam-product mixture is directly sprayed into a steam-drying chamber. The product can be dried therein with superheated steam, instead of with dry air. This process is referred to as steam drying. It has been found that a very favorable process management is obtained, if a pasteurization/sterilization nozzle according to the invention is combined with a steam-drying device.

Preferably, this is done in such a manner that, as regards the used steam, a substantially closed system is realized. This means that (a part of the) used steam is recirculated. The part of the steam that condenses during the process will generally be discharged from the steam-drying device. The superheated steam is passed through the drying chamber and ensures that water evaporates from the product. After leaving the drying chamber, the steam (with the steam coming from the product) can again be compressed and heated to the desired degree of superheating, and the resulting superheated steam can be returned to the drying chamber, preferably at a location in the direct vicinity of the pasteurization/sterilization nozzle. Consequently, the required drying energy is much lower than when conventionally drying with dry air, which cannot be reused so easily. The conditions of drying are selected subject to the product. Those skilled in the art are deemed to reach a suitable optimization on the basis of their normal expert knowledge. In most of the cases the temperature will range between 150 and 500° C.

It may be clear that the quality of the injected steam has to be in accordance with the required quality of the product to be dried. For the steam drying of, for instance, a food the injected steam has to be food grade, and therefore in essence free from mineral oil, moisture droplets, microorganisms, and dirt.

The steam drying according to the invention has the additional advantage that because of the fact that steam is already introduced into the mixing chamber of the nozzle, atomization and pasteurization or sterilization takes place simultaneously, and in a substantially closed system the excess steam can be reused for atomization. On the other hand, it also turns out that such a steam drying method is very suitable for steam drying a product in liquid form that is atomized in the mixing chamber while admixing steam and is sprayed into a steam-drying chamber and dried with superheated steam. Preferably, the steam coming from the drying chamber again is reused again, after it has been superheated again.

Optionally, a product partially dried through drying can be redried to a lower moisture content in a conventional manner, such as, for instance, with a fluid bed-drying device.

The combination of pasteurization or sterilization and steam drying or conventional spray drying can be excellently carried out using an above-described nozzle, such as, for instance, shown in FIG. 1. For a best possible atomization in the drying chamber the outflow opening preferably narrows conically. In a preferred embodiment, the diameter at the end of the outflow opening is maximally 6 mm, for instance about 4-5 mm, or even smaller. If a greater passage capacity is desired, there is the possibility to use a number of nozzles parallel to each other.

Moreover, it has turned out that in a powder dried according to the invention undesired organoleptic changes have been hardly effected, if effected at all, and that a powder dried according to the invention has sufficient solubility for various applications. A method according to the invention is thus suitable for preparing a product consumable without health risks, optionally after reconstitution in a suitable liquid.

Furthermore, the invention can be used for the manufacture of consumption products or other powdered products that, besides heat-sensitive components, also contain starch and many other food ingredients. In methods according to the state of the art, these products are often prepared by dissolving all the desired components, while selecting pregelatinized starch as a source for the starch. This has the disadvantage that the starch has to be pregelatinized in a separate process step, which increases the risk of microbiological infection.

It has now been found that moreover, by using a method according to the invention, in which germs are killed and the activity of heat-sensitive substances, if present, can be retained, native starch in a product with many food ingredients can be gelatinized to a substantial degree, so that the product becomes suitable for human consumption. It has turned out that such a pasteurized or sterilized and optionally dried product prepared according to the invention has a suitable microbiological quality. It has also been found after evaluation of a product that during drying according to the invention much fewer undesired reactions, such as excessive polymerization, oxidation, reduction, irreversible denaturation, and the like, take place than when using conventional techniques. As far as during the use of a method according to the invention denaturation and/or polymerization take place, this is the case to a much lesser degree than in a conventional method for a similar product in which a similar decimal reduction of the germ count is realized. Moreover, in a preferred embodiment, the possibly occurring denaturation is reversible for a substantial part, or at least less irreversible denaturation occurs than in a conventional method.

With a method according to the invention, a product can be obtained having a relatively very good wettability and dissolution behavior. In a preferred embodiment, a dried powdered product obtained according to the invention consists of small particles having an average diameter of not more than 60 μm, which is less than the average particle size when using conventional spray drying techniques, in which the diameter is mostly more than 100 μm. These small particles are also referred to as primary particles. In a preferred embodiment, it is possible to obtain a powdered product the primary particles of which have an average size in the range of 10-60 μm. In another preferred embodiment, the primary particles have an average size of 20-50 μm. The desired diameter depends on the nature of the product and may, if desired, also be smaller or larger.

These primary particles can be formed by selecting the conditions such that during atomization small droplets are formed, for instance through a high pressure in the mixing chamber, realizable in various manners, such as through a high steam flow/product flow ratio and/or a small diameter of the outflow opening. Small droplets are rapidly dried after leaving the mixing chamber via the spray nozzle, while a rapid cooling of the droplets proves to take place, which is an important advantage for reaching a best possible microbiological quality of the product.

The primary powder particles in a product according to the invention can form, during drying, agglomerates characteristic of the invention. By forming such agglomerates the solubility of a product can be improved. The forming of agglomerates in a method according to the invention can be stimulated by carrying out the spray drying in a device in which the outflow openings of a number of nozzles are directed towards each other, so that the outflowing sprays intermix. Such a technique is also referred to as InterSpray Mixing, in which at least part of the primary product particles agglomerate. In a special embodiment thereof, a device comprising a double-walled tube is used, in which the sprays from the inner and outer tube mix together. In the central inner tube, spraying according to the invention takes place. Via the outer tube, particles can be added to a second flow, during which an intensive mixing occurs.

It has been found that the agglomeration proceeds better by utilizing a number of nozzles according to the invention than in a conventional drying process with high-pressure nozzles. Without limiting the invention thereto, it is believed that this is probably also due to the manner of occurring atomization, in which the agglomeration also takes place in the mixing area where steam/product sprays from different nozzles meet. Furthermore, in comparison with drying through hot air, in a preferred embodiment of a steam-drying process according to the invention, small particles remain relatively wet on the outside as a result of the steam present, which may lead to a degree of stickiness, so that the colliding product particles agglomerate.

In a preferred embodiment, the agglomerated particles are separated from the non-agglomerated and small particles. It has now been found that to this end, for instance, a conventional cyclone is useful. The non-agglomerated particles can then be returned, in a preferred embodiment, via one or more nozzles to a steam-drying chamber and still agglomerate with other particles.

The agglomerates are preferably formed from the primary particles. Depending on the product and the method parameters, the size of the agglomerates can be adjusted. As a rule, it is advantageous to realize agglomerates with a largest possible size. The size of the agglomerates may be up to 200 μm or more.

The invention will now be illustrated further with reference to some examples.

EXAMPLE 1

A product having the following composition was prepared by pasteurizing and atomizing a slurry with a two-fluid nozzle (see FIG. 1) with internal pasteurization chamber. Then the atomized product was dried in a spray tower.

| Composition (wt. % on the basis of solids) | |
|---|---|
| Fats | 33.4% |
| Proteins | 23.6% |
| of which: | |
| whey | 18.9% |
| casein | 4.4% |
| Carbohydrates (lactose) | 35.0% |
| Vitamins & minerals | 8.0% |
| Process conditions | |
| Solid content slurry | 55% |
| Temperature slurry | 60° C. |
| Steam pressure | 14 bar |
| Product throughput | 250 kg/h |
| Volume pasteurization chamber | 17 ml |
| Outflow opening nozzle | 5 mm |
| Process quality | |
| Aerobic germ count slurry at 30° C. | 80,000 /g |
| Aerobic germ count product at 30° C. | <200 /g (after drying) |
| Moisture content product | <4% (after drying) |

EXAMPLE 2

A product having the following composition was prepared by pasteurizing and atomizing a slurry with a two-fluid nozzle (see FIG. 1) with internal pasteurization chamber. Then the atomized product was dried in a spray tower.

| Composition (wt. % on the basis of solids) | |
|---|---|
| Fats | 27.4% |
| Proteins | 11.6% |
| of which: | |
| whey | 9.3% |
| casein | 2.3% |
| Carbohydrates | 54.2% |
| of which: | |
| lactose | 34.8% |
| glucose | 0.1% |
| polysaccharides | 6.3% |
| starch | 13.0% |
| Vitamins & minerals | 6.8% |
| Process conditions | |
| Solid content slurry | 50% |
| Temperature slurry | 63° C. |
| Steam pressure | 12 bar |
| Product throughput | 230 kg/h |
| Volume pasteurization chamber | 20 ml |
| Outflow opening nozzle | 6 mm |
| Process quality | |
| Aerobic germ count slurry at 30° C. | 35,000 /g |
| Aerobic germ count product at 30° C. | <200 /g (after drying) |
| Moisture content product | <4% (after drying) |

The invention claimed is:

1. A method for pasteurizing or sterilizing a product in liquid form which includes a heat sensitive substance comprising:

substantially atomizing the product in liquid form by admixing steam in a mixing chamber heated by the steam so as to kill microorganisms and produce a pasteurized or sterilized product wherein the product in liquid form has a solid content of at least 53 wt. %;

the steam is introduced into the mixing chamber using a spray nozzle, at a steam pressure of between about 3 bar and 20 bar;

the temperature in the mixing chamber is between about 120° C. and 250° C.;

the residence time of the product in the mixing chamber is between about 0.2 msec and 20 msec; and the weight ratio between the product in liquid form and steam is between about 1.6 and 10; and drying the pasteurized or sterilized product into powder form.

2. The method of claim 1, wherein the mixing chamber has a length of between about 1 cm and 20 cm.

3. The method of claim 1, wherein the steam is introduced into the mixing chamber at a steam pressure of between about 5 bar and 15 bar.

4. The method of claim 1, wherein one or more products are selected from the group consisting of peptides, proteins, fats, vitamins, antioxidants, minerals, hormones, steroids, polysaccharides, vegetable oils, and sugars.

5. The method of claim 1, wherein the pasteurized or sterilized product leaves the mixing chamber through an outflow opening having a size of less than 6 mm.

6. The method of claim 1, wherein the pasteurized or sterilized product leaves the mixing chamber through an outflow opening having a size of less than 5 mm.

7. The method of claim 1, wherein the weight ratio between the product in liquid form and steam is between about 1.75 and 7.

8. The method of claim 1, wherein the temperature in the mixing chamber is between about 120° C. and 150° C.

9. The method of claim 1, wherein the product in liquid form is a stable emulsion.

10. The method of claim 1, wherein the pasteurized or sterilized product is injected into an expansion vessel.

11. The method of claim 10, wherein the expansion vessel is a flash system.

12. The method of claim 1, wherein the pasteurized or sterilized product leaving the mixing chamber flows into a drying chamber in which the product is dried.

13. The method of claim 12, wherein at least a part of the supplied steam, after leaving the drying chamber, is superheated and returned to the drying chamber.

14. The method of claim 12, wherein the dried product contains an agglomerate of primary powder particles.

15. The method of claim 14, wherein the product is dried using at least two nozzles, wherein outflow openings of the nozzles are arranged such that outgoing sprays comprising product and steam contact each other.

16. The method of claim 15, wherein non-agglomerated primary particles are recirculated to the drying chamber via at least one of the spray nozzles.

17. The method of claim 1, wherein a decimal reduction of at least 2 is reached.

18. The method of claim 1, wherein the solid content is 0.7-6.5 kg per kg steam.

19. The method of claim 1, wherein the mixing chamber has inflow openings that are placed such that the steam flow and the product flow enter the mixing chamber in substantially parallel direction.

20. The method of claim 1, wherein the mixing chamber has at least one inflow opening for the steam that contains a steam distribution plate.

21. The method of claim 1, wherein the steam is brought near the product concentrically around an inflow opening of product in the mixing chamber.

22. The method of claim 1, wherein the product comprises proteins, fats, minerals, and carbohydrates.

23. The method of claim 1, wherein the steam is atomized in the mixing chamber.

* * * * *